United States Patent [19]

Alvarez

[11] 4,261,986

[45] Apr. 14, 1981

[54] 4-HALO ETIANIC ACIDS AND DERIVATIVES THEREOF

[75] Inventor: Francisco Alvarez, Sunnyvale, Calif.

[73] Assignee: Syntex (U.S.A.) Inc., Palo Alto, Calif.

[21] Appl. No.: 95,762

[22] Filed: Nov. 19, 1979

Related U.S. Application Data

[63] Continuation-in-part of Ser. No. 70,478, Aug. 29, 1979, Pat. No. 4,228,279, and Ser. No. 893,643, Apr. 5, 1978, abandoned.

[51] Int. Cl.$^3$ .................... C07J 71/00; A61K 31/56
[52] U.S. Cl. .................... 424/243; 260/397.1; 260/397.45; 260/239.55 D; 260/239.5
[58] Field of Search .................... 260/397.1; 424/238, 424/243

[56] References Cited

U.S. PATENT DOCUMENTS

| | | | |
|---|---|---|---|
| 3,232,960 | 2/1966 | Magerlein et al. | 260/397.1 |
| 3,707,537 | 12/1972 | Kierstead et al. | 260/397.1 |
| 4,093,721 | 6/1978 | Phillipps et al. | 260/397.1 |

*Primary Examiner*—Elbert L. Roberts
*Attorney, Agent, or Firm*—Kate H. Murashige; Tom M. Moran

[57] ABSTRACT

Certain 3-oxoandrost-4-ene and 3-oxoandrosta-1,4-diene 17β-carboxylic acids and esters substituted at the 4-position with a fluoro or chloro and optionally substituted at the six position with fluoro or chloro are useful as anti-inflammatory steroids. These compounds are optionally substituted at the 9α-position with fluoro, chloro or bromo; substituted at the 11 with a keto, a β-hydroxy or a β-chloro (the latter only when there is a 9α-chloro); substituted at 16α (or 16β) with methyl or hydrogen, and at 17α with hydroxy or an ester.

11 Claims, No Drawings

4-HALO ETIANIC ACIDS AND DERIVATIVES THEREOF

This is a continuation-in-part of applications Ser. No. 893,643, filed Apr. 5, 1978, now abandoned, and Ser. No. 070,478, filed Aug. 29, 1979 now U.S. Pat. No. 4,228,279.

BACKGROUND OF THE INVENTION

1. Field of the Invention

This invention relates to novel $\Delta^4$-3-oxo-etianic acids which are substituted at the 4-position with fluoro, chloro or bromo and are optionally substituted at the 6-position with fluoro or chloro and at the 9-position with fluoro, chloro or bromo. The compounds are active anti-inflammatory agents in mammals. The invention further relates to pharmaceutically active compositions comprising a compound of the invention in combination with pharmaceutically acceptable excipient. The invention also relates to a process for preparing the compounds of the invention.

2. Prior Art

It is known that $\Delta^4$-3-keto-etianic acids which are substituted at the 9 position with chlorine or fluorine and at the 11 position with keto or hydroxy or chloro group. See for example U.S. Pat. No. 3,828,080 to Phillipps. In addition certain 4-fluoro and 4-chloro substituted steroids of the pregnane series are known. See, for example, U.S. Pat. No. 3,232,960 to Magerlein and U.S. Pat. No. 3,707,537 to Kierstead. It is also known that certain 3-keto-etianic acids and esters may be substituted at both the $9\alpha$ and $6\alpha$ positions with fluoros. See for example, U.S. Pat. No. 4,093,721 to Phillipps and U.S. Pat. No. 3,036,010 to Anner.

A heretofore unknown series of $\Delta^4$-3-keto-etianic acids being substituted at the 4 position with fluoro, chloro or bromo has been discovered and is disclosed herein. The compounds exhibit superior anti-inflammatory activity as compared to other etienic acid derivatives which are already known.

SUMMARY OF THE INVENTION

One aspect of this invention is a compound chosen from those represented by the formula

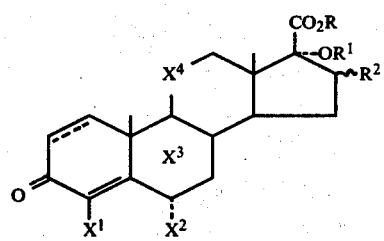

(I)

wherein
$X^1$ is fluoro or chloro;
$X^2$ is fluoro, chloro or hydrogen;
$X^3$ is fluoro, chloro, bromo or hydrogen;
$X^4$ is =C=O or

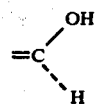

or may be

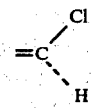

when $X^3$ is choro;
R is hydrogen, alkyl of 1 through 6 carbon atoms, optionally substituted with one halo substituent, or phenyl or benzyl optionally substituted with one substituent chosen from the group consisting of alkyl of 1 through 4 carbon atoms, alkoxy of 1 through 4 carbon atoms and halo;
$R^1$ is hydrogen or alkanoyl of 2 through 6 carbon atoms;
$R^2$ is hydrogen, $\alpha$-methyl or $\beta$-methyl; and
the solid and broken lines between C-1 and C-2 represent a single or double bond.

Another aspect of this invention is a topical anti-inflammatory pharmaceutical composition which comprises at least one suitable pharmaceutical excipient in combination with an effective amount of a compound chosen from those represented by Formula (I), above, wherein each of the substituents are as defined, with the proviso that R is not hydrogen. Particularly valuable compounds in this composition are set forth hereafter.

Still another aspect of this invention is a process for treating an inflamed condition in mammals which comprises treating the afflicted mammals which comprises treating the afflicted mammal with an effective amount of a compound chosen from those represented by Formula (I), above, wherein substituents are as defined above, with the proviso that R is not hydrogen.

Still further aspects of this invention include processes for preparing the novel compounds of the invention and are set forth hereafter.

DETAILED DESCRIPTION

Compounds

In its broadest aspect, this invention is a compound chosen from those represented by Formula I wherein
$X^1$ is fluoro or chloro;
$X^2$ is fluoro, chloro or hydrogen;
$X^3$ is fluoro, chloro, bromo or hydrogen;
$X^4$ is =C=O or

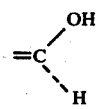

or may be

when $X^3$ is chloro;
R is hydrogen, alkyl of 1 through 6 carbon atoms optionally substituted with one halo substituent, or phenyl or benzyl optionally substituted with 1 substituent chosen from the group consisting of alkyl of 1 through 4 carbon atoms, alkoxy of 1 through 4 carbon atoms and halo;

R¹ is hydrogen or alkanoyl or 2 through 6 carbon atoms;
R² is hydrogen, α-methyl or β-methyl; and
the solid and broken lines between C-1 and C-2 represent a single or double bond.

One subgroup of the broad aspect of the invention comprises those compounds represented by Formula (I) wherein
X¹ is fluoro or chloro;
X² is fluoro or hydrogen;
X³ is fluoro, chloro or hydrogen;
X⁴ is

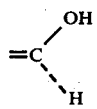

or may also be

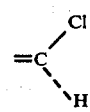

when X is chloro;
R is alkyl of one through six carbon atoms, halo-alkyl of one or two carbon atoms, phenyl or benzyl;
R¹ is alkanoyl of two through six carbon atoms; and
R² is hydrogen, α-methyl or β-methyl.

Of these a preferred subgroup comprises those compounds of Formula (I), wherein X¹ is fluoro; X² and X³ are independently hydrogen or fluoro; X⁴ is

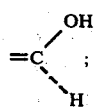

R is methyl, fluoromethyl or fluoroethyl; R¹ is acetyl or propionyl; and R² is α-methyl or β-methyl. Preferably, there is a double bond between C-1 and C-2.

In defining the compounds of this invention alkyl of 1 through 6 carbon atoms includes both straight chain and branched alkyl groups such as methyl, ethyl, n-propyl, isopropyl, n-butyl, isobutyl, t-butyl, pentyl, isoamyl, n-hexyl and the like. Haloalkyl of 1-6 carbon atoms refers to an alkyl which is substituted with a halogen atom such as fluorine, chlorine, bromine or iodine and includes such groups as fluoromethyl, chloromethyl, 2-fluoroethyl, 2-chloroethyl, 3-fluoropropyl and the like. The phenyl and benzyl substituents may be substituted on the phenyl ring at the 2, 3 or 4 positions with one substituent such as hydroxy, alkoxy of 1-4 carbon atoms (e.g. methoxy, ethoxy, n-propoxy and the like), alkyl of 1-4 carbons (e.g. methyl, ethyl, isopropyl, n-propyl, t-butyl, n-butyl, etc), or a halo such as fluoro, chloro, bromo or iodo. Preferably the substitution is at the 2 or 4 positions. Alkanoyl of 2 through 6 carbon atoms refers to a group of the formula

where R⁴ is alkyl of 1 through 5 carbon atoms, e.g. acetyl, propionyl, butyryl, valeryl, caproyl and the like.

In naming the compound of this invention the substituents present on the androstane ring shall be included alphabetically and the compounds shall be alkyl (or phenyl or benzyl) 17β-carboxylates. For example, if in Formula (I), above, X¹ and X² are fluoro, X³ and X⁴ are chloro, R is methyl, R¹ is acetoxy and R² is α-methyl the name is methyl 17α-acetoxy-9α,11β-dichoro-4,6α-difluoro-16α-methyl-3-oxoandrosta-1,4-diene-17β-carboxylate. If, on the other hand, R is hydrogen but X¹, X², X³, X⁴, R¹ and R² are the same the compound is named 17α-acetoxy-9α,11β-dichloro-4,6α-difluoro-16α-methyl-3-oxoandrosta-1,4-diene 17β-carboxylic acid.

Process For Preparing The Compounds Of The Invention

The compounds of the invention are ultimately obtained by a process of this invention.

In one process a 17α-hydroxy-17β-carboxylate or 17β-carboxylic acid is converted to the corresponding 17α-ester by esterifying the 17α hydroxy with a suitable acid or reactive derivative thereof. In another process, the 17β-carboxylates are obtained by esterifying the corresponding 17β-carboxylic acid or a reactive derivative thereof. In still another process a Δ⁵-4α-halo compound is converted into the corresponding Δ⁴-4-halo compound. And finally, the 17β-carboxylic acids of the invention are prepared by oxidizing the corresponding 21-hydroxy (or 21-ester)-20-oxopregn-4-ene with a suitable oxidizing agent.

An overall process for preparing some of the compounds of the invention may be viewed as a two-part procedure which may be carried out in any order. One part is to eliminate the 21 carbon atom from a 21-hydroxy (or 21-ester)-pregnane and the other part is to fluorinate or chlorinate at the 4 position. These two processes may be represented by the following reaction sequences:

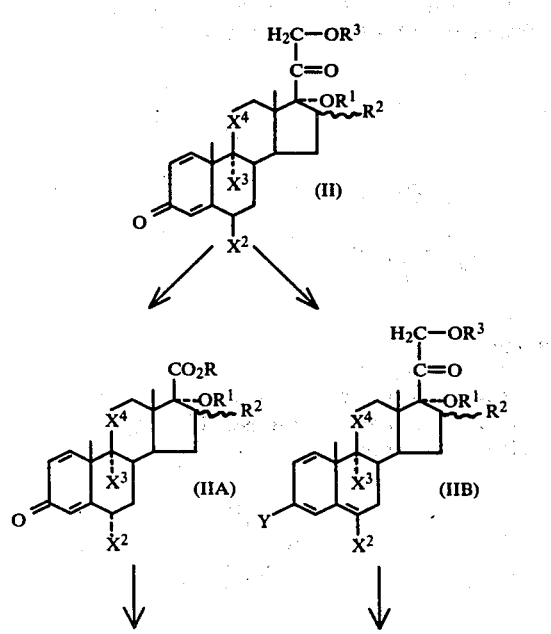

-continued

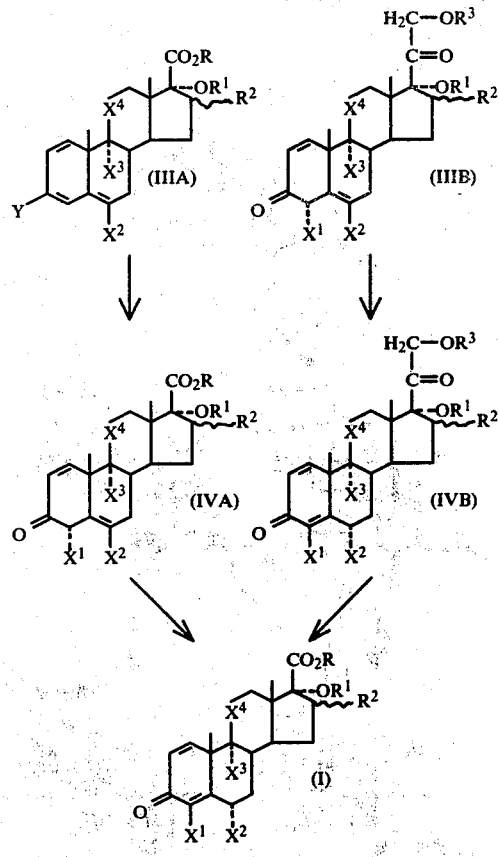

wherein R, $R^1$, $R^2$, $X^1$, $X^2$ and $X^4$ are as previously defined, $R^3$ is hydrogen or alkanoyl of one through six carbon atoms and $X^3$ is fluoro or chloro.

As is apparent from the reaction sequence, the fluorination or chlorination (referred to collectively as "halogenation") at the 4-position is a three step process while the elimination of the 21-carbon atom is essentially a one step process.

If a compound of Formula (II) is a 17α,21-dihydroxy steroid and the "B" series of intermediates are formed, it is preferably reacted with acid aqueous formaldehyde to form the 17α,21; 20-21-bis-methylene-dioxy of the Formula (II) below. Thus both the 17 and 21 hydroxy moieties are protected from reaction. Thereafter, intermediates represented by Formulas (II'B), (III'B), (IV'B) and (V'B) are prepared according to the following reaction sequence:

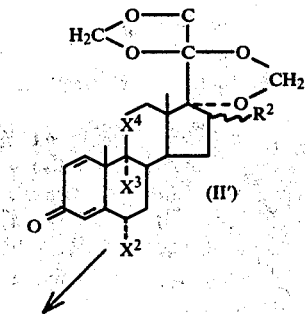

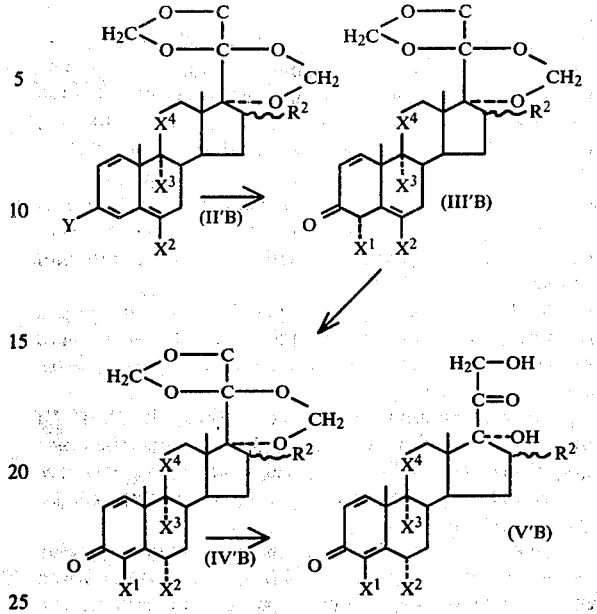

If the compound of Formula (II) is a 17α,21-dihydroxy steroid and the "A" series of intermediates are formed, then, after the 21 carbon is eliminated, the 17α-hydroxy substituent is protected by forming a 17α-alkanoyloxy of two through six carbon atoms ($R^1O$) and a lower alkyl ester of 1–6 carbons of the 17β-carboxylic acid is formed.

Once the hydroxy groups are appropriately protected, the first step of the halogenation process is performed. A compound represented by (II), (II') or (IIA) is reacted to form a compound of the Formula (IIB), (II'B) or (IIIA), respectively, wherein Y is a protecting group such as an alkoxy, particularly methoxy. This is carried out by reacting, for example, a large molar excess of trimethyl orthoformate in methanol in the presence of a catalytic amount (i.e. less than 5% by weight) of a suitable acid catalyst such as fuming sulfuric acid at reflux temperature or less. About 50°–55° C. is preferred. Generally the molar ratio of trimethyl orthoformate to steroid is about 10:1 to about 30:1. Once the reaction is complete a base is added to neutralize the acid and the resulting product represented by Formula (IIB), (II'B) or (IIIA) is recovered and purified using methods well known in the art such as evaporation, recrystallization, etc.

The compound represented by Formula (IIB), (II'B) or (IIIA) is then halogenated using perchlorylfluoride ($ClO_3F$) or trifluoromethoxy fluoride ($CF_3OF$) as a fluorinating agent or a source of positive chlorine such as N-chlorosuccinimide, dichlorohydantoin, etc. as a chlorinating agent to form the 3-keto-4α-fluoro (chloro)-$\Delta^{1,5}$ steroid represented by Formula (IIB), (III'B) or (IVA).

In the case of $ClO_3F$, which is a gas, an approximately equimolar amount, i.e. about 1 to 1.1 moles $ClO_3F$ per mole compound of Formula (IIB), (II'B) or (IIA) is metered into a mixture of the compound in a solution which is a major amount of acetone, preferably 90% by weight, and a minor amount of water, preferably about 10%, over a period of about 1–3 hours at 10°–30° C., preferably ambient temperatures. Dichlorohydantoin is reacted using a solvent such as acetone and water or tetrahydrofuran and water to dissolve one of the reactants and adding the solution to the compound in a similar solvent.

A compound of Formula (IIIB), (III′B) or (IVA), in turn, is reacted with a suitable base such as an alkali metal carbonate, e.g. potassium carbonate, in a suitable oxygenated hydrocarbon solvent such as an alkanol, e.g. methanol, and an inert atmosphere at 10°–50° C. (preferably ambient) to convert the $\Delta^5$-compound III′B to form the desired 4-fluoro(4-chloro)-$\Delta^{1,4}$-3-ketone. This "last step" conversion is a novel process for preparing a compound of this invention, e.g. the compound of Formula I.

The BMD protecting group is hydrolyzed using a suitable acid such as 60% formic acid, 80% acetic acid or 48% hydrofluoric acid according to procedures known in the art.

Once a compound represented by Formula (I), (IVB) or (V′B), i.e. is obtained a $\Delta^{1,4}$-3-keto steroid, the compound may be readily selectively hydrogenated at the 1–2 bond by any of the means known in the art to obtain the corresponding $\Delta^4$-3-keto steroid.

The elimination of a 21 carbon atom from a suitable pregnane can be accomplished by any means known in the art such as using sodium hypobromide as taught in U.S. Pat. No. 2,769,822. Alternatively, a suitable pregnane represented by Formula (IVB) or (V′B) can be oxidized to the corresponding 17β-carboxylic acid with periodic acid, in a solvent medium and preferably at room temperature or with sodium bismuthate of the 17α-acyloxy pregnane compound. As will be appreciated should the starting pregnane compound contain any substituent sensitive to the above described oxidation, such groups should be suitable protected.

Preferably the oxidation is accomplished by using a suitable inorganic base such as an alkali metal carbonate in an oxygenated hydrocarbon derivative (alcohol) and in the presence of oxygen.

Thus, the conversion of a compound of Formula (IVB) or (V′B) into a compound of formula (I) is carried out in a suitable oxygenated hydrocarbon solvent such as a lower alkanol. Particularly valuable and, therefore preferred are methanol and ethanol, particularly the former. The reaction medium is made slightly basic by the inclusion of a suitable weak inorganic base such as an alkali metal carbonate, for example sodium, lithium or potassium carbonate. Potassium carbonate is preferred. The conversion of a compound of formula (I) to a compound of formula (II) takes place at temperatures of about 10° C. to about the boiling of the solvent being employed, e.g., about 75° C. for ethanol and about 50° C. for methanol. Generally, however, the reaction readily takes place from ambient temperatures, i.e., about 20° C.–25° C.

An important aspect of the process of this invention is the presence of oxygen during the reaction. Oxygen can be supplied to the reaction mixture by a variety of ways. For example the reaction mixture can be stirred vigorously in a reaction vessel open to the air so that air is mixed with the reaction mixture. This is relatively inefficient however, thus it is preferred that oxygen be injected into the reaction mixture. This is readily accomplished by bubbling a stream of air or oxygen, preferably the former, into the reaction mixture while it is being stirred. The reaction at ambient temperatures will be complete about 1 to 48 hours, depending on the reactants. Less time is required at higher temperatures.

If $X^3$ in the compound represented by Formula (II) is hydrogen, then one of the following reaction sequences is carried out:

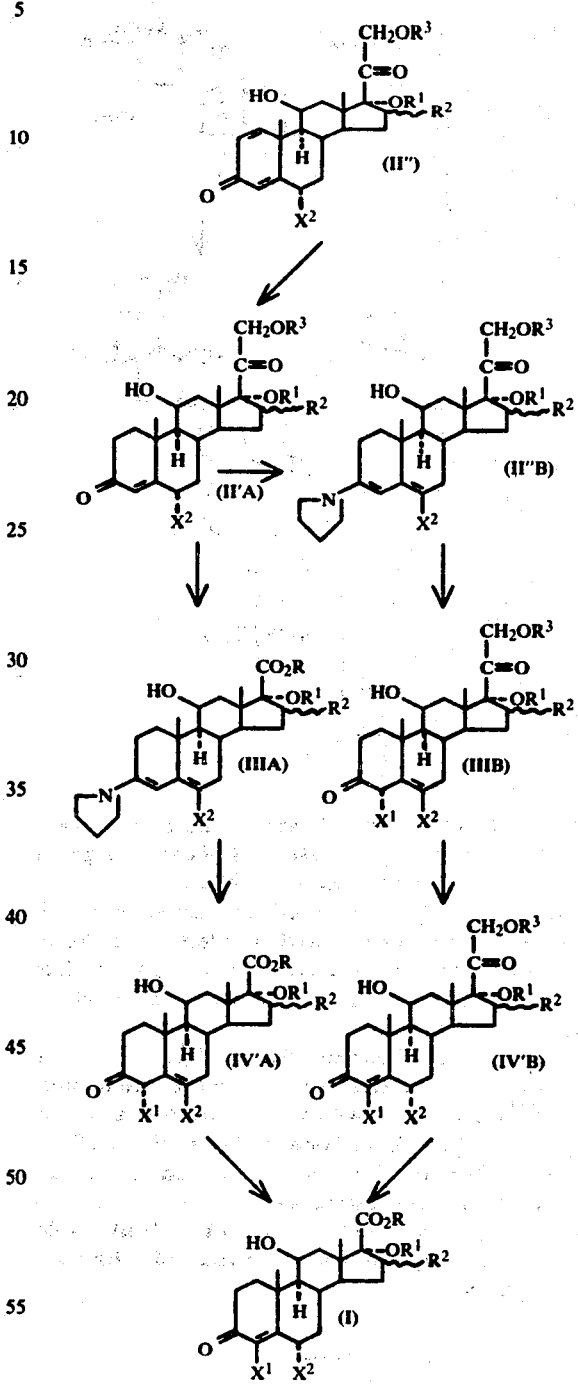

wherein $X^1$, $X^2$, R, $R^1$, $R^2$ and $R^3$ are as defined hereinbefore.

Of course, the hydroxy groups are appropriately protected as discussed above, if necessary. In converting a compound represented by Formula (II″) to the enamine represented by (III″A) or (II″B), (II″) is reacted with a suitable amine such as pyrrolidine, in a solvent such as benzene at reflux temperature until the reaction is completed.

The other steps in the reaction sequence immediately above are in essence discussed hereinbefore.

The parent 17β-carboxylic acids of compounds of Formula (I) may be esterified in known manner to provide 17β-carboxylate esters according to the invention. For example, in order to prepare a lower alkyl ester the 17β-carboxylic acid may be reacted with an appropriate diazoalkane, e.g. diazomethane, the reaction being preferably performed in a solvent medium, e.g. ether, tetrahydrofuran or methanol, and at a low temperature, preferably at −5° to +30° C. Alternatively, the 17β-carboxylic acid may be reacted with an appropriate O-alkyl-N,N'-dicyclohexylisourea, e.g. O-t-butyl-N,N'-dicyclohexyl isourea, preferably in an aprotic solvent such as ethyl acetate, and advantageously at a temperature of 25°-100° C. Alternatively, salt of the parent 17β-carboxylic acid for example, an alkali metal, e.g. lithium, sodium or potassium, salt or a quaternary ammonium, e.g. triethyl ammonium or tetrabutyl ammonium, salt may be reacted with an appropriate alkylating agent, for example, an alkyl, phenyl or benzyl halide, e.g. the iodide, or a dialkyl sulfate, e.g. dimethylsulphate, preferably in a polar solvent medium such as acetone, methylethyl ketone or dimethyl formamide, conveniently at a temperature in the range 25°-100° C. The reaction with an alkyl halide may conveniently be employed to prepare the ethyl and propyl 17β-carboxylate esters and higher alkyl esters according to the present invention.

The esterification of the 17α-hydroxy group in the above-described preparation of the new androstane compounds may be effected by reacting the parent 17α-hydroxy compound with an appropriate carboxylic acid, advantageously in the presence of trifluoroacetic anhydride and preferably in the presence of an acid catalyst, e.g. p-toluene-sulphonic acid or sulphosalicylic acid.

The reaction is advantageously effected in an organic solvent medium such as benzene, methylene chloride or an excess of the carboxylic acid employed, the reaction being conveniently effected at a temperature of 20°-100° C.

Alternatively, the 17α-hydroxy group may be esterified by reaction of the parent 17α-hydroxy compound with a suitable reactive derivative of an appropriate acid, e.g. the appropriate acid anhydride or acid chloride, if desired, in the presence of non-hydrolytic solvents, e.g. chloroform, methylene chloride or benzene, and preferably in the presence of a strong acid catalyst, e.g. perchloric acid, p-toluene sulphonic acid or a strong acidification exchange resin, e.g. Amberlite IR 120, the reaction being conveniently effected at a temperature of 25° to 100° C.

For the preparation of 17α-esters of the 17β-carboxylic acids which may be employed in the preparation of the compounds according to the invention, it is often preferred to treat the parent 17α-hydroxy compounds with the appropriate carboxylic acid anhydride to give the 17α-ester of the mixed anhydride of the androstane 17β-carboxylic acid and the carboxylic acid of the starting anhydride, this reaction being conveniently effected at an elevated temperature, the resulting anhydride then being solvolysed under acidic conditions (e.g. under aqueous acetic acid) or under basic conditions (e.g. under aqueous pyridine or a secondary amine such as diethylamine in acetone).

Those compounds of Formula (I) wherein R represents a lower alkyl group substituted by a halogen atom may be prepared, for example, by reacting a salt of the parent 17β-carboxylic acid with an appropriate halo compound (RZ where R is as previously defined and Z is halogen such as chlorine, bromine or iodine) serving to introduce the desired group R in the compound of Formula (I).

This reaction is advantageously effected using as the salt of the parent 17β-carboxylic acid an alkali metal, e.g. lithium, sodium or potassium, salt or a quaternary ammonium salt such as the triethylammonium or tetrabutylammonium salt, conveniently in a polar solvent such as acetone, methylethyl ketone or dimethyl formamide.

Compounds of Formula (I) wherein R represents a lower alkyl group substituted by a halogen atom at the carbon atom attached to the oxygen atom of the 17β-carboxylate may be prepared, for example, by reacting the parent 17β-carboxylic acid with an appropriate aldehyde in the presence of a hydrohalic acid. The reaction may advantageously be carried out in the presence of a catalyst, for example zinc chloride.

The starting materials, represented by Formula (II) wherein $X^4$ is

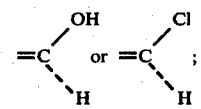

$X^1$ is fluoro, chloro or bromo; $X^2$ is fluoro or chloro; $X^3$ is hydrogen and R is OH are readily prepared by starting with compounds known in the art and proceeding according to the following reaction sequence:

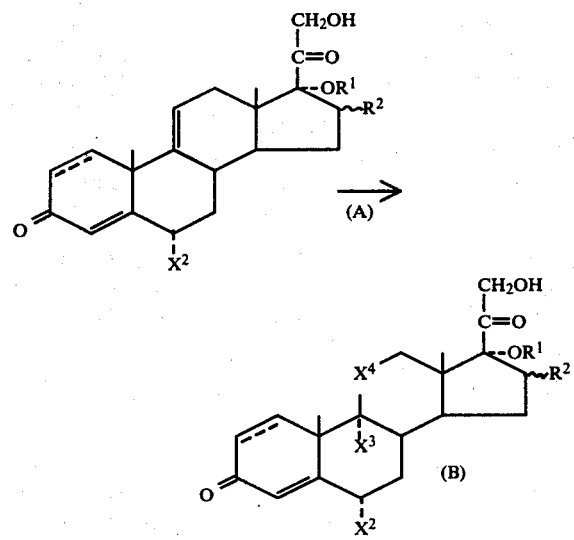

The pregna-1,4,9(11)-triene-3,20-diones of formula (A) are known or can readily be repared by treating a known 11β-hydroxy steroid (see Progress in Drug Research, Vol. 5, E. Jucher, Ed., 1963, for example) in dimethylformamide and pyridine and reacting with methanesulfonyl chloride at room temperature for 20-24 hours, then extracting with methylene chloride and recovering according to the process set forth in Example 3A of U.S. Pat. No. 3,009,933 to Robinson.

The pregna-1,4,9(11)-trienes represented by formula (A) above are converted to various intermediates by means known in the art. For example they are treated with chlorine according to the process of U.S. Pat. No. 3,009,933 to give the corresponding 9α,11β-dichloropregna-1,4-diene

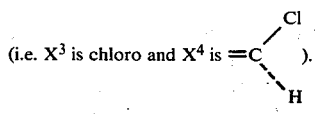

(i.e. $X^3$ is chloro and $X^4$ is $=C\diagup^{Cl}_{\diagdown H}$ ).

The 9α-fluoro-11β-hydroxy compound is prepared by reacting the appropriate pregna-1,4,9(11) triene with dibromohydantoin to form the 9α-bromo-11-hydroxypregna-1,4-diene which in turn is reacted with sodium hydroxide to give the corresponding 9β,11β-epoxide. This epoxide is then treated with a hydrogen fluoride/urea complex according to the process set forth in U.S. Pat. No. 3,211,758 to Tarkoey to give the 9α-fluoro-11β-hydroxy compound. The 9α-chloro-11β-hydroxy compound is prepared by reacting the 9β,11β-epoxide with hydrogen chloride in methylene chloride or by reacting the $\Delta^{9,(11)}$ steroid with dichlorohydrantoin. An 11β-hydroxy (9-unsubstituted) steroid is readily prepared by methods well known in the art such as employing *Cunninghamella blakesleena, Cunninghamella bainieri, Curvularia lunata* or other suitable micro-organisms in a suitable medium which selectively affords the desired 11-hydroxy steroid.

For further reference to compounds represented by formula (A) or (B), see U.S. Pat. No. 3,126,375; U.S. Ser. No. 711,042, filed Aug. 2, 1976; U.S. Pat. No. 2,997,4890; Edwards et al. JACS 82, 2318 (1969).

Administration and Formulation

The compounds of Formula (I) where R is alkyl of 1-6 carbon atoms, haloalkyl of 1-6 carbons or phenyl or benzyl optionally substituted on the phenyl ring with alkyl of 1-4 carbons, alkoxy of 1-4 carbons or halo and $R^1$, $R^2$, $X^1$, $X^2$, $X^3$ and $X^4$ are as defined in the broadest aspect of the invention are useful for the relief of inflamed conditions in mammals, and more specifically are useful for relieving inflammatory manifestations of corticosteroid responsive dermatoses. Initial approximation of anti-inflammatory activity is done by following the procedure of McKenzie, S. W. and Stoughton, R. B., "Methods for Comparing Percutaneous Absorption of Steroids" Arch Dermat, 86, (1962) or modifications thereof.

Generally, the inflammatory manifestation in a mammal, particularly humans, is combatted by administering to the afflicted mammal a therapeutically effective amount of the novel steroids of this invention, that is an amount which results in improvement of the inflamed condition. Preferably the steroids are first formulated to prepare a suitable pharmaceutical formulation, as discussed hereinafter, which is then placed in contact with the afflicted area. An effective amount will depend upon he particular condition and the mammal receiving the treatment but will vary between 0.001% to 10% by weight of the pharmaceutical composition and preferably will be between 0.01 and 1% by weight of the formulation. Using these levels in the formulation, a therapeutically effective and non-side effect producing amount, i.e. enough to effect an anti-inflammatory response, but not enough to adversely effect the recipient, is applied to the inflamed area.

The compounds of this invention not only have anti-inflammatory activity but also exhibit a low level of systemic activity, as measured by recognized laboratory assays. This allows for the application of an effective amount of the anti-inflammatory compounds with little adverse effect on the rest of the mammal's system.

The novel steroids of this invention may be formulated with suitable pharmaceutical excipients known in the art to form particularly effective anti-inflammatory compositions which are administered orally, nasally, rectally, or, preferably, topically. Generally an effective amount of the steroid is about 0.001%w to about 10%w of the total formulated composition. The rest of the formulated composition will be about 90%w to about 99.999%w of suitable excipients which may include a pharmaceutically acceptable solvent and other pharmaceutically acceptable additives to form an effective pharmaceutical formulation.

A pharmaceutically acceptable solvent is one which is substantially non-toxic and non-irritating under the conditions used and may be readily formulated into any of the classical drug formulations such as powders, creams, ointments, lotions, gels, foams, suppositories, aerosols, solutions or the like. Particularly suitable solvents include water, glycerine, propylene carbonate, and aglycol such as 1,2-propylene diol (i.e. propylene glycol), 1,3-propylene diol, polyethylene glycol having a molecular weight of from 100 to 10,000, dipropylene glycol, etc.; and mixtures of the aforementioned with each other.

A topical cream may be prepared as a semi-solid emulsion of oil in water or water in oil. A cream gase formulation by definition is an emulsion which is a two-phase system with one liquid (for example fats or oils) being dispersed as small globules in another substance (e.g., a glycol-water solvent phase) which may be employed as the primary solvent for the novel steroids therein, the cream formulation may contain fatty alcohols, surfactants, mineral oil or petrolatum and other typical pharmaceutical adjuvants such as anti-oxidants, antiseptics, or compatible adjuvants. A typical cream base formulation is given in the following table:

| Water/glycol mixture (15% or more glycol) | 50-99 parts by weight |
|---|---|
| Fatty alcohol | 1-20 |
| Non-ionic Surfactant | 0-10 |
| Mineral oil | 0-10 |
| Typical pharmaceutical adjuvants | 0-5 |
| Active Ingredients | 0.001-10 |

The fatty alcohol, non-ionic surfactant, and other adjuvants are discussed in U.S. Pat. No. 3,934,013 to Poulsen which is incorporated herein by reference.

The novel steroids of this invention may also be formulated as ointments. A "classical" ointment is a semi-solid anhydrous composition which may contain mineral oil, white petrolatum, a suitable solvent such as a glycol and may include propylene carbonate and other pharmaceutically suitable additives such as surfactants, for example Span and Tween, or wool fat (lanolin), along with stabilizers such as antioxidants and other adjuvants as mentioned before. Following is an example of a typical "classical" ointment base:

| White petrolatum | 50-94 parts by weight |
|---|---|
| Mineral Oil | 5-20 |
| Glycol solvent | 1-15 |
| Surfactant | 0-10 |

| | |
|---|---|
| Stabilizer | 0-10 |
| Active Ingredients | 0.001-10.0 |

Other suitable ointment base formulations which employ propylene carbonate are described in a copending U.S. Pat. No. 4,017,615 issued Apr. 12, 1977 by Shastri et al entitled "Propylene Carbonate Ointment Vehicle" and U.S. Pat. No. 3,924,004 issued Dec. 2, 1975 by Chang et al entitled "Fatty Alcohol-Propylene Carbonate-Glycol Solvent Cream Vehicle". As much of those applications as is pertinent is incorporated herein by reference. Following is a typical ointment base formulation containing propylene carbonate:

| | |
|---|---|
| Active Ingredients | 0.001-10.0 parts by weight |
| Propylene Carbonate | 1-10 |
| Solvent | 1-10 |
| Surfactant | 1-10 |
| White Petrolatum | 70-97 |

Suitable solvents, surfactants, stabilizers, etc. are discussed in U.S. Pat. No. 3,934,013 and such discussion is incorporated herein by reference.

A suitable "non-classical" anhydrous, water washable "ointment type" base is described in U.S. Pat. No. 3,592,930 to Katz and Neiman, and that patent is incorporated hereby by reference. A representative composition of this invention utilizing such a base is as follows:

| | |
|---|---|
| Glycol solvent | 40-35 parts by weight |
| Fatty alcohol | 15-45 |
| Compatible plasticizer | 0-15 |
| Compatible coupling Agent | 0-15 |
| Penetrant | 0-20 |
| Active Ingredients | 0.001-10.0 |

By following the procedures set forth above for preparing the starting material for the compounds of this invention, steroids of a relatively simple structure can be converted to other structures as desired. Thus, exemplary known compounds which can be employed to prepare starting materials for compounds of this invention according to procedures discussed above include progesterone, corticosterone, hydrocortisone, prednisolone, betamethasone, dexamethasone, triamcinolone, paramethasone, fluocinolone, triamcinolone acetonide, fluocinolone acetonide, and the like.

Further specific embodiments of this invention are found in the following examples which are given by way of illustration only and are not to be interpreted as limiting the scope of the claims appended hereto.

EXAMPLE 1

This example sets forth a process for preparing 4,6α,-9α-trifluoro-11β,17α-dihydroxy-16α-methyl-3-oxoandrosta-1,4-diene-17β-carboxylic acids and the corresponding alkyl, phenyl or benzyl 17β-carboxylate derivatives as well as the corresponding 17α-alkanoyloxy derivatives according to the following reaction sequence:

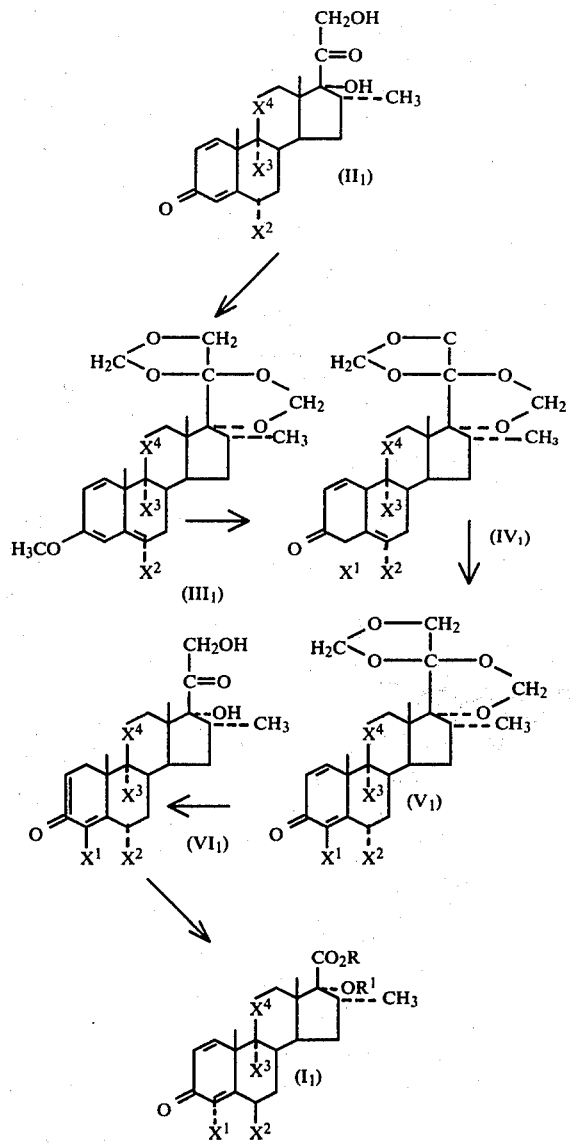

A. Preparation of 4,6α,9α-trifluoro-11β,17α-dihydroxy-16α-methyl-3-oxoandrosta-1,4-diene-17β-carboxylic acid Eight grams (g) of flumethasone (6α,9α-difluoro-11β,17α,21-trihydroxy-16α-methylpregna-1,4-diene-3,20-dione) is stirred into 200 milliliters (ml) of chloroform and 50 g of warm parafomaldehyde, and 120 ml of concentrated hydrochloric acid in 120 ml of water are added thereto. The mixture is stirred for 48 hours at ambient temperature and the two layers are separated. The aqueous layer is extracted with chloroform, and the combined organic layer and chloroform extracts are washed to neutrality, dried over sodium sulfate and evaporated to dryness to yield the 18α, 20:20,21-bis-methylenedioxy (BMD) derivative of flumethasone which is recrystallized from methanol:ether.

Forty-one g of the BMD derivative of flumethasone prepared according to the preceeding paragraph is added to a solution of 620 ml trimethyl orthoformate, 206 ml anhydrous methanol, and 4.1 ml fuming sulfuric acid. The resulting mixture is warmed to 40°-50° C. for 30 minutes, at which time thin layer chromatography (TLC) using an eluant of 35% ethyl acetate and 65% hexane shows that the reaction is complete. Twenty-five ml of triethyl amine are added to neutralize the acid and the solvents are removed using a rotary evaporator at reduced pressure. The residue is dissolved in 500 ml of acetone, about 240 ml water is added and the acetone is removed under reduced pressure to give a crystalline precipitate which is collected by filtration and air dried overnight to give 40 g of compound (III$_1$), above which is crystallized from methanol-water.

Ten g of the resulting product are added to 300 ml of a solvent consisting of 90%w acetone and 10%w water and a slow stream (about 1 mole) of perchloryl fluoride (ClO$_3$F) is added at ambient temperature over about 30 minutes. TLC of the reaction mixture using an eluant of 35% ethyl acetate and 65%w hexane shows the reaction to be complete upon completion of the ClO$_3$F addition. Water is slowly added to the reaction mixture until a total volume of 2 liters (l) is obtained. The mixture is concentrated under reduced pressure to give a crystalline precipitate which is collected by filtration, dissolved in methylene chloride (CH$_2$Cl$_2$) and the resulting solution is dried over anhydrous sodium sulfate. The solution contains the product represented by (IV$_1$), which is purified by chromatography on silica gel using a hexane methylene chloride solvent mixture. One g of the resulting product is stirred with 200 ml methanol and 20 ml CH$_2$Cl$_2$ containing 200 milligrams (mg) of anhydrous potassium carbonate in an inert atmosphere (nitrogen) at atmospheric pressure and ambient temperature for one hour, at which time TLC shows the reaction is complete. The rection mixture is diluted with 20 ml methanol and 2 ml glacial acetic acid and concentrated under reduced pressure to a small volume. The crystalline precipitate which forms is collected by filtration and washed with methanol and water to give 0.9 g of the product represented by formula (V$_1$), namely the 17α,20; 20,21-bismethylenedioxy derivative 4,6α,9α-trifluoro-11β,17α,21-trihydroxy-16α-methylenepregna-1,4-diene-3,20-dione.

The resulting product (V$_1$) (0.5 g) is added to a mixture of 3 g of urea/4 g liquid hydrofluoric acid and 2 ml of water. The mixture is stirred at room temperature for 2 hours at which time TLC using 5% methanol-95% dichloromethane shows the reaction to be complete. The reaction mixture is then diluted with 100 ml of water, and the crystalline precipitate of the resulting product is collected by filtration and dried to give 0.3 g of a product represented by formula (VI$_1$), namely 4,6α,9α-trifluoro-11β,17α,21-trihydroxy-16α-methyl-pregna-1,4-diene-3,20-dione.

Ten g of (VI$_1$) prepared in this manner is mixed with 200 ml methanol and 2 g anhydrous potassium carbonate (K$_2$CO$_3$) and stirred at ambient temperature and atmospheric pressure while a slow current of air is bubbled through the reaction mixture for 22 hours. Methanol is added at periodic intervals to maintain a constant volume. The reaction mixture is diluted with water to give a total volume of 0.5 l, then concentrated under reduced pressure to about 15 ml hydrochloric acid is added slowly while stirring until a pH of 2 is obtained. The resulting crystalline precipitate is collected by filtration and air dried to give a compound represented by formula (I$_1$) where both R and R$^1$ are hydrogen, namely 4,6α,9α-trifluoro-11β,17α-dihydroxy-16α-methyl-3-oxoandrosta-1,4-diene-17β-carboxylic acid.

B. Preparation of 17α-alkanoyloxy-4,6α,9α-trifluoro-11β-hydroxy-16α-methyl-3-oxoandrosta-1,4-diene 17β-carboxylic acids The product according to Part A of this example is mixed with 5 ml of pyridine and 5 ml of propionic anhydride and stirred for three hours at ambient temperature. The resulting mixture is slowly diluted with water to a volume of 200 ml, stirred at ambient temperature for one hour, and the resulting precipitate is collected by filtration to give a compound represented by formula (I$_1$) where R is hydrogen and R$^1$ is propionyl, namely 4,6α,9α-trifluoro-11β-hydroxy-16α-methyl-3-oxo-17α-propionyloxyandrosta-1,4-diene 17β-carboxylic acid.

Similarly, by substituting acetic anhydride, butyric anhydric, valeric anhydride or caproic anhydride for propionic anhydride, the following compounds are prepared:

17α-acetoxy-4,6α,9α-trifluoro-11β-hydroxy-16α-methyl-3-oxoandrosta-1,4-diene 17β-carboxylic acid;

17α-n-butyryloxy-4,6α,9α-trifluoro-11β-hydroxy-16α-methyl-3-oxoandrosta-1,4-diene 17β-carboxylic acid;

4,6α,9α-trifluoro-11β-hydroxy-16α-methyll-3-oxo-16α-valeryloxyandrosta-1,4-diene 17β-carboxylic acid; and 4,6α,9α-trifluoro-17α-n-hexanoyloxy-11β-hydroxy-16α-methyl-3-oxo-17α-valeryloxyandrosta-1,4-diene 17β-carboxylic acid.

C. Preparation of alkyl or benzyl 17α-alkanoyloxy 4,6α,9p-trifluoro-11β-hydroxy-16α-methyl-3-oxoandrosta-1,4-diene 17β-carboxylates One g of 4,6α,9α-trifluoro-11β-hydroxy-16α-methyl-3-oxo-17α-propionyloxyandrosta-1,4-diene 17β-carboxylic acid, prepared in step B, above, is dissolved in 10 ml of dimethylformamide (DMF) and 1 g sodium bicarbonate and 1 g methyl iodide is added. This mixture is stirred at ambient temperature for 48 hours. The mixture is diluted with water to a volume of 0.3 l and the resulting crystalline precipitate is collected by filtration, dissolved in 500 ml of CH$_2$Cl$_2$, dried over anhydrous sodium sulfate and filtered through a column of 200 g silica gel, eluting first with Ch$_2$Cl$_2$ then with Ch$_2$Cl$_2$ containing 2,4,6 and 10%w ethyl acetate. The eluates are combined and concentrated to dryness under reduced pressure to yield a compound represented by formula (I$_1$) where R is methyl and R$^1$ is propionyl, namely methyl 4,6α,9α-trifluoro-11β-hydroxy-16α-methyl-3-oxo-17α-propionyloxyandrostan-1,4-diene 17β-carboxylate, mp 240°–256° C., [α]$_D$10° (CHCl$_3$).

Similarly by following in principle this procedure but substituting other alkyl iodides or benzyl iodides for methyl iodide other alkyl or benzyl carboxylates are prepared such as ethyl 4,6α,9α-trifluoro-11β-hydroxy-16α-methyl-3-oxo-16α-propionyloxyandrosta-1,4-diene 17β-carboxylate;

2-chloroethyl 4,6α,9α-trifluoro-11β-hydroxy-16α-methyl-3-oxo-16α-propionyloxyandrosta-1,4-diene 17β-carboxylate;

2-fluoroethyl 4,6α,9α-trifluoro-11β-hydroxy-16α-methyl-3-oxo-16α-propionyloxyandrosta-1,4-diene 17β-carboxylate;

isopropyl 4,6α,9α-trifluoro-11β-hydroxy-16α-methyl-3-oxo-16α-propionyloxyandrosta-1,4-diene 17β-carboxylate;

n-propyl 4,6α,9α-trifluoro-11β-hydroxy-16α-methyl-3-oxo-16α-propionyloxyandrosta-1,4-diene 17β-carboxylate;

t-butyl 4,6α,9α-trifluoro-11β-hydroxy-16α-methyl-3-oxo-16α-propionyloxyandrosta-1,4-diene 17β-carboxylate;

n-pentyl 4,6α,9α-trifluoro-11β-hydroxy-16α-methyl-3-oxo-16α-propionyloxyandrosta-1,4-diene 17β-carboxylate;

benzyl 4,6α,9α-trifluoro-11β-hydroxy-16α-methyl-3-oxo-16α-propionyloxyandrosta-1,4-diene 17β-carboxylate;

4-chlorobenzyl 4,6α,9α-trifluoro-11β-hydroxy-16α-methyl-3-oxo-16α-propionyloxyandrosta-1,4-diene 17β-carboxylate;

2-fluorobenzyl 4,6α,9α-trifluoro-11β-hydroxy-16α-methyl-3-oxo-16α-propionyloxyandrosta-1,4-diene 17β-carboxylate;

3-methylbenzyl 4,6α,9α-trifluoro-11β-hydroxy-16α-methyl-3-oxo-16α-propionyloxyandrosta-1,4-diene 17β-carboxylate;

4-n-propylbenzyl 4,6α,9α-trifluoro-11β-hydroxy-16α-methyl-3-oxo-16α-propionyloxyandrosta-1,4-diene 17β-carboxylate;

4-ethoxybenzyl 4,6α,9α-trifluoro-11β-hydroxy-16α-methyl-3-oxo-16α-propionyloxyandrosta-1,4-diene 17β-carboxylate; and 4-methoxybenzyl 4,6α,9α-trifluoro-11β-hydroxy-16α-methyl-3-oxo-16α-propionyloxyandrosta-1,4-diene 17β-carboxylate.

Similarly, by substituting the other 17α-alkanoyloxy compounds prepared in part B of this example for 4,6α,9α-trifluoro-11β-hydroxy-16α-methyl-3-oxo-17α-propionlyoxyandrosta-1,4-diene carboxylic acid and other alkyl iodides or benzyl iodides still other compounds of this invention are prepared such as ethyl 17α-acetoxy-4,6α,9α-trifluoro-11β-hydroxy-16α-methyl-3-oxoandrosta-1,4-diene 17β-carboxylate;

t-butyl 17α-acetoxy-4,6α,9α-trifluoro-11β-hydroxy-16α-methyl-3-oxoandrosta-1,4-diene 17β-carboxylate; and benzyl 17α-acetoxy-4,6α,9α-trifluoro-11β-hydroxy-16α-methyl-3-oxoandrosta-1,4-diene 17β-carboxylate.

D. Preparation of alkyl or benzyl 4,6α,9α-trifluoro-11β,17α-dihydroxy-16α-methyl-3-oxoandrosta-1,4-diene 17α-carboxylate By following in principle the procedure of Part C of this example but substituting 4,6α,9α-trifluoro-11β,17α-dihydroxy-16α-methyl-3-oxoandrosta-1,4-diene 17β-carboxylic acid for the corresponding 17α-propionyloxy compound, a compound of formula ($I_1$) are prepared wherein $R^1$ is hydrogen and R is methyl, ethyl, propyl, butyl, benzyl, or monosubstituted benzyl.

EXAMPLE 2

This example sets forth a process for preparing 9α,11β-dichloro-4,6α-difluoro-17α-hydroxy-16α-methyl-3-oxoandrosta-1,4-diene 17β-carboxylic acids, the corresponding alkyl, phenyl or benzyl 17β-carboxylates, and the corresponding 17α-alkanoyloxy derivatives.

A. Preparation of methyl 9α,11β-dichloro-4,6α,difluoro-16α-methyl-3-oxo-17α-propionyloxyandrosta-1,4-diene 17B-carboxylate Ten g 9α,11β-dichloro-6α-fluoro-17α,21-dihydroxy-16α-methyl-pregna-1,4-diene-3,20-dione is mixed with 100 ml methanol and 10 g anhydrous potassium carbonate ($K_2CO_3$) and stirred for 22 hours at ambient temperature and atmospheric pressure while slow current of air is bubbled through the reaction mixture. Methanol is added at periodic intervals to maintain a constant volume. The reaction mixture is diluted with water to give a total volume of 250 ml then concentrated hydroxhloric acid is added slowly while stirring until a pH of 2 is obtaiaed. The resulting crystalline precipitate is collected by filtration and air dried to give 8 g of a compound represented by Formula ($IIA_1$), namely 9α,11β-dichloro-6α-fluoro-16α-hydroxy-16α-methyl-3-oxoandrosta-1,4-diene 17β-carboxylic acid.

The resulting compound 5 g is mixed with 25 ml of pyridine and 25 ml of propionic anhydride and stirred for three hours at ambient temperature. The resulting mixture is slowly diluted with water to a volume of 1000 ml, stirred at ambient temperature for one hour, and the resulting precipitate is collected by filtration to yield a compound represented by Formula ($IIA_1$) where $R^1$ is propionyl, namely 9α,11β-dichloro-6α-fluoro-16α-methyl-3-oxo-17α-propionyloxyandrosta-1,4-diene 17β-carboxylic acid.

Five g of 9α,11β-dichloro-6α-methyl-3-oxo-17α-propionyloxyandrosta-1,4-diene 17β-carboxylic acid of this product are dissolved in 50 ml of dimethylformamide (DMF). Five G $NaHCO_3$ and 5 g $CH_3I$ are added and the mixture is reacted for 10 hours at ambient temperature. Water is added to give a volume of 3 l and the resulting crystalline precipitate is collected by filtration, dissolved in 500 ml of $CH_2Cl_2$, dried over anhydrous sodium sulfate and filtered through a column of 200 g silica gel, eluting first with $Ch_2Cl_2$ then with $CH_2Cl_2$ containing 2,4,6 and 10% (v/v) ethyl acetate. The eluates are combined and concentrated to dryness under reduced pressure to yield a compound represented by Formula (IIA) where R is methyl and $R^1$ is propionyl, namely methyl 9α-11β-dichloro-6α-difluoro-16α-methyl-3-oxo-17α-propionyloxyandrostan-1,4-diene 17β-carboxylate.

To a solution of 620 ml trimethyl orthoformate, 206 ml anhydrous methanol, and 4.1 ml fuming sulfuric acid is added 41 g of the product prepared according to the preceeding paragraph. The resulting mixture heated to 50°–55° for 30 minutes, at which time thin layer chromatography (TLC) using an eluant of 35% ethyl acetate and 65% hexane shows that the reaction is complete. Twenty-five ml of triethyl amine are added to neutralize the acid and the solvents are removed using a rotary evaporator at reduced pressure. The residue is dissolved in 500 ml of acetone, about 240 ml water is added and the acetone is removed under reduced pressure to give crystalline precipitate which is collected by filtration and air dried overnight to give 40 g of compound represented by Formula ($IIIA_1$), above.

The resulting product (30 g) is added to 300 ml of a solvent consisting of 90%w acetone and 10% water and (1.0 mole) of perchloryl fluoride ($ClO_3F$) are added at ambient temperature over about 30 minutes. TLC of the reaction mixture using an eluant of 35% ethyl acetate and 65% hexane shows the reaction to be complete upon completion of the $ClO_3F$ addition. Water is slowly added to the reaction mixture until a total volume of 2.1 is obtained. The mixture is concentrated under reduced pressure, and the precipitate obtained is dissolved in CH$_2$Cl$_2$, dried over anhydrous Na$_2$SO$_4$, and filtered through a column of 400 g of silica gel using 70% CH$_2$Cl$_2$/30% hexane.

The homogeneous fractions are combined, concentrated to dryness to give 22 g of the product represented by (IVA$_1$).

The resulting product (1 g) is stirred with 20 ml methanol and 20 ml CH$_2$Cl$_2$ containing 200 milligrams (mg) of anhydrous potassium carbonate in an inert atmosphere (nitrogen) at atmospheric pressure and ambient temperature for one hour, at which time TLC shows the reaction is complete. The reaction mixture is diluted with 20 ml methanol and 2 ml glacial acetic acid and concentrated under reduced pressure to a small volume, then diluted with water. The crystalline precipitate which forms is collected by filtration and washed with methanol and water to give 0.9 g of the product represented by Formula (I$_1$), namely methyl 9α,11β-dichloro-4,6α-difluoro-16α-methyl-3-oxo-17α-propionyloxyandrosta-1,4-diene 17β-carboxylic acid.

B. Preparation of alkyl or benzyl 17α-alkanoyloxy-9α,11β-dichloro-4,6α-difluoro-11β-hydroxy-16α-methyl-3-oxoandrosta-1,4-diene 17β-carboxylates Similarly by following in principle this procedure but substituting other alkyl iodides or benzyl iodides for methyl iodide and other anhydrides such as acetic anhydride, n-butyric anhydride, caproic anhydride, and the like for propionic anhydride in the preparatin of the compound represented by (IIA$_1$), above, other alkyl or benzyl carboxylates are prepared such as
ethyl 9α,11β-dichloro-4,6α-difluoro-16α-methyl-3-oxo-17α-propionyloxyandrosta-1,4-diene 17β-carboxylate
benzyl 17α-butyryloxy-9αα,11β-dichloro-4,6α-difluoro-16α-methyl-3-oxoandrosta-1,4-diene 17β-carboxylate; and the like.

EXAMPLE 3

This example sets forth a process for preparing 9α-bromo-4,6α-difluoro-11β,17α-dihydroxy-16α-methyl-3-oxoandrosta-1,4-diene 17β-carboxylic acid and the corresponding 17α-alkanoyloxy derivatives as well as the alkyl or benzyl 17β-carboxylates.

A. By following in principle the appropriate procedure set forth in Part A of Example 2, but substituting 6α-fluoro-17α,21-dihydroxy-16α-methylpregna-1,4,9(11)-triene-3,20-dione for 9α,11β-dichloro-6α-fluoro-17α,21-dihydroxy-16α-methylpregna-1,4-diene-3,20-dione, a compound represented by (IIA$_1$) is prepared wherein R is methyl and R$^1$ is propionyl, namely, methyl 6α-fluoro-16α-methyl-3-oxo-17α-propionyloxyanodrosta-1,4,9(11)-triene 17β-carboxylate. This compound, in turn, is treated with dibromohydantoin or dichlorohydantoin by methods known in the art to yield methyl 9α-bromo-4,6α-difluoro-11β-hydroxy-16α-methyl-3-oxo-17α-propionyloxyandrosta-1,4-diene 17β-carboxylate or the corresponding 9α-chloro compound represented by formula (IIA$_1$). This compound, in turn is readily fluorinated according to principles set forth in Part A of Example 2.

B. By following in principle the procedure of Part A of this example but substituting other suitable anhydrides for propionic anhydride and other alkyl or benzyl iodides for methyl iodide, other alkyl or benzyl 17α-akanoyl 17β-carboxylates are prepared, for example
methyl 9α-bromo-4,6α-difluoro-11β-hydroxy-16α-methyl-3-oxo-17α-propionyloxyandrosta-1,4-diene 17β-carboxylate;
ethyl 9α-chloro-4,6α-difluoro-16α-methyl-3-oxo-17α-acetoxy androsta-1,4-diene 17β-carboxylate;
n-pentyl 9α-bromo-4,6α-difluoro-11β-hydroxy-16α-methyl-3-oxo-17α-propionyloxy androsta-1,4-diene 17β-carboxylate; and the like.

EXAMPLE 4

By following in principle the appropriate procedure set forth in Examples 1, 2 or 3 but using an appropriate starting material and substituting n-chlorosuccinimide for perchloryl fluoride, the alkyl or benzyl 17α-alkanoyloxy-4-chloro-6α-fluoro-16α-methyl-3-oxoandrosta-1,4-diene 17β-carboxylates of formula (I) are prepared wherein X$^1$ is chloro, X$^2$ is fluoro, X$^3$ is fluoro, chloro or bromo and X$^4$ is

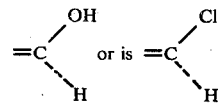

when X$^3$ is chloro, such as
ethyl 4,9α,11β-trichloro-6α-fluoro-16α-methyl-3-oxo-17α-propionyloxyandrosta-1,4-diene 17β-carboxylate;
methyl 4,9α-dichloro-6α-fluoro-11β-hydroxy-16α-methyl-3-oxo-17α-propionyloxyandrosta-1,4-diene 17β-carboxylate; and
n-propyl 4,9α-dibromo-6α-fluoro-11β-hydroxy-16α-methyl-3-oxo-17α-propionyloxyandrosta-1,4-diene 17β-carboxylate; and the like.

EXAMPLE 5

By following in principle the procedures set forth in Examples 1–4 but substituting the corresponding 16β-methyl steroids for the 16α-methyl steroids, 4-fluoro-17α-hydroxy-16β-methyl-3-oxoandrosta-1,4-diene 17β carboxylic acid and the corresponding 17α-alkanoyloxy derivatives as well as the corresponding alkyl, phenyl or benzyl 17β-carboxylates are prepared, for example
methyl 4,6α,9α-trifluoro-17α-hexanoyloxy-11β-hydroxy-16β-methyl-3-oxoandrosta-1,4-diene 17β-carboxylate;
methyl 4,6α,9α-trifluoro-11β-hydroxy-16β-methyl-3-oxo-17α-propionyloxyandrosta 1,4-diene 17β-carboxylate;
flluoroethyl 4,6α-difluoro-11β-hydroxy-16β-methyl-3-oxo-17α-propionyloxyandrosta-1,4-diene 17β-carboxylate;

B. The 17α-alkanoyloxy derivatives of the compounds of Part A of this example are prepared by following in principle the process of Part B of Example 2 but using the starting materials of Part A of this Example. For example the 17α-acetoxy, -propionyloxy, -n-butyryloxy, secondary butyryloxy or hexanoyloxy derivatives are prepared.

C. By following in principle the procedure set forth in Part C of Example 2 the corresponding alkyl, benzyl or phenyl 17α-carboxylates of the compound prepared in Part B of this example may be prepared such as phenyl-4-fluoro-11β-hydroxy-16β-methyl-3-oxo-17α-propionyloxyandrosta-1,4-diene 17β-carboxylate;

benzyl 9α,11β-dichloro-4-fluoro-16β-methyl-3-oxo-17α-propionyloxyandrosta-1,4-diene 17β-carboxylate;

n-pentyl 9α,11β-dichloro-4-fluoro-16α-methyl-3-oxo-17α-propionyloxyandrosta-1,4-diene 17α-carboxylate; and the like.

EXAMPLE 6

This example sets forth a process for preparing 4-chloro-17α-hydroxy-16α-methyl-3-oxo-androsta-1,4-diene 17β-carboxylic acid and the corresponding 17α-alkanoyloxy derivatives as well as the alkyl, benzyl or phenyl 17β-carboxylates according to the following reaction sequence wherein $X^1$ is chloro $X^3$ is fluoro, chloro or bromo and $X^4$ is

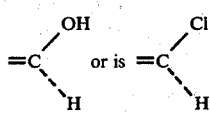

when $X^3$ is chloro.

A. By following in principle the procedure set forth in Part A of Example 1 and substituting chlorohydantoin for perchloryl fluoride, the following compounds are prepared such as 4-chloro-9α-fluoro-11β,17α-dihydroxy-16α-methyl-3-oxoandrost-4-ene 17β-carboxylate;

hexyl 17α-acetoxy-4-chloro-9α-fluoro-11β-hydroxy-16α-methyl-3-oxo-17α-propionyloxyandrost-4-ene 17β-carboxylate; and the like.

EXAMPLE 7

By following in principle the procedures set forth in Examples 1-6 but substituting the corresponding 16-unsubstituted steroid starting material for the 16α-methyl or 16β-methyl steroid starting material, the corresponding 16-unsubstituted steroids of this invention are obtained, such as 4,6α,9α-trifluoro-11β,17α-dihydroxy-3-oxoandrosta-1,4-diene 17-carboxylic acid and the corresponding 17β-alkanoyloxy derivatives along with the corresponding alkyl or benzyl 17β-carboxylates.

EXAMPLE 8

This example sets forth a process for making Δ⁴ steroids of this invention.

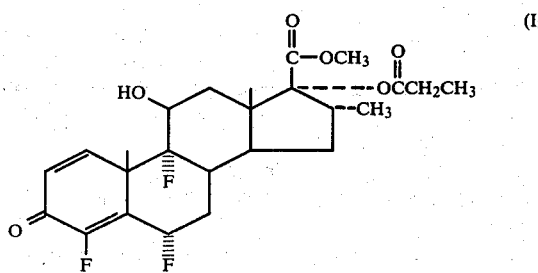

A solution of 25 mg of tris-(triphenylphosphine) chlororhodium in 6 ml of benzene and 15 ml of ethanol is stirred under hydrogen for 60 minutes. 244 Mg of 4,6α,9α-trifluoro-11β,17α-dihydroxy-16α-methyl-3-oxoandrosta-1,4-diene-17β-carboxylic acid, represented by formula (I₈), is added and the resulting solution is stirred under hydrogen at room temperature at atmospheric pressure. After 48 hours final hydrogen uptake is complete, and the solution is evaporated to dryness and the residue taken up in a mixture of petroleum ether and methylene chloride. The pure product is isolated by column chromatography on silica gel to give 4,6α,9α-trifluoro-11β,17α-dihydroxy-16α-methyl-3-oxoandrostan-4-ene-17β-carboxylic acid.

Similarly, by substituting other $\Delta^{1,4}$ steroids of this invention made according to Examples 1-4 and 8-10 for the compound of formula (I₈), other corresponding $\Delta^4$ steroids are prepared.

EXAMPLE 9

This example sets forth a process for preparing an 11-keto compound of this invention by oxidizing any of the 11-hydroxy steroids set forth in Examples 1-8.

One g. of methyl 4,6α,9α-trifluoro-11β-hydroxy-16α-methyl-3-oxo-17α-propionyloxyandrosta-1,4-diene 17β-carboxylate is dissolved in 50 ml of acetone and treated at room temperature with Jone's reagent (chromic anhydride in dilute sulfuric acid) dropwise until TLC indicates the absence of starting material. The mixture if treated with five drops of isopropyl alcohol to destroy any excess of reagent, then diluted with 50 ml of water and the mixture concentrated under vacuum under reduced pressure to give a crystalline material, namely methyl 5,6α,9α-trifluoro-16α-methyl-3,11-dioxo-17α-propionyloxyandrosta-1,4-diene carboxylate.

Similarly by substituting other 11-hydroxy steroids prepared in Examples 1 and 3-8 for methyl 4,6α,9α-trifluoro-11β-hydroxy-16α-methyl-3-oxo-17α-propionyloxyandrosta-1,4-diene 17β-carboxylate, other 11-keto steroids of this invention are prepared.

EXAMPLE 10

LD₅₀

Six Swiss-Webster mice (Simonsen) each weighing about 25 grams, were injected subcutaneously with a solution of methyl 6α,9α-difluoro-11β-hydroxy-16α-methyl-3-oxo-17α-n-propionyloxyandrosta-1,4-diene 17β-thiocarboxylate in carbomethoxycellulose having a concentration of 10 ml/kg. The dosage was 25 mg/kg or about 0.625 mg/mouse. The mice were observed daily for mortality for 21 days. One mouse died. The LD₅₀ is, therefore, more than 25 mg/kg.

EXAMPLE 11

Biological Activity

This example sets forth data for the topical anti-inflammatory and thymolytic activities of methyl 4,6α,9α-trifluoro-11β-hydroxy-16α-methyl-3-oxo-17α-propionyloxyandrosta-1,4-diene 17β-carboxylate of this invention.

The topical anti-inflammatory activity potential for each compound was assayed using a modified Stoughton/-McKenzie vaso-constriction assay in humans, V. A. Place, et al, *Arch. Dermat.* 101, 531–537 (1970). Eight normal adult human subjects were treated on each forearm by topical administration with alcohol solutions containing $1 \times 10^{-5}$ and $1 \times 10^{-6}$ g/ml of each of the compounds to provide 64 total test sites for each compound in a series (32 for each concentration). Areas of the subjects' forearms were outlined by a rubber stamp grid coated with silicone grease, and 10 microliters are applied per 7×7 mm square site. After the preparations have dried, the areas on each forearm are covered with Saran ® wrap and the margins sealed with tape. The occlusive wrap is removed after 18 hours. Twenty-four hours after application, the presence of vasoconstriction is noted by visual examination, and expressed as the number of sites responding (vasoconstriction). Fluocinolone acetonide is used as a standard. Also, the intensity of the vasoconstriction is scorred on a 0, 1, 2 scale, 2 being the most intense reaction. Both scores are used in constructing dose-response graphs according to methods set forth in an article by V. A. Place et al, infra.

The compounds to be tested for thymolytic activity including a hydrocortisone (HC) standard, were prepared in three or more concentrations by suspension in a sodium carboxymethyl-cellulose vehicle. Animals received the test materials by subcutaneous injection of 0.5 ml of the suspension on each of three successive days. Four hours following the final injection, the rats were sacrificed and the thymus gland of each animal removed and weighed. These weights are then employed to establish dose-response graphs by methods known in the art. The compound tested showed slight activity in the dose range of hydrocortisone (the standard).

Overall, the compound shows excellent topical potency (1-2 time FA) with little systemic activity (only 10 times HC) and thus exhibit a distinct therapeutic advantage. Other compounds of the invention have a similar therapeutic advantage over art compounds.

EXAMPLE 12

In this example a formulation is prepared of the following composition

|  | % w/w |
|---|---|
| Methyl 4,6α,9α-trifluoro-11β-hydroxy-16α-methyl-3-oxo-17α-propionyloxyandrosta-1,4-diene 17β-carboxylate | 0.025 |
| Stearyl Alcohol | 30.0 |
| PEG 6000 | 5.0 |
| 1,2,6-Haxanetriol | 2.5 |
| Citric Acid Anhydrous, USP | 0.02 |
| Propylene Glycol, USP, q.s. | 100.0 |

The steroid is dissolved in 624.8 grams of propylene glycol at 90°–95° C. The latter is then mixed with the other ingredients at 80°–85° C. to give the desired formulation.

EXAMPLE 13

This example sets forth an alternate method of preparing the β-methyl steroids of this invention.

A. Ten (10) g of 6α-fluoro-16β-methyl-17α,21-diacetoxypregna-1,4,9(11)-triene-3,20-dione in 110 mls of dioxane (A.R.) plus 2.2 mls of a solution of 4.4 mls 70% HClO$_4$ in 200 mls of water is treated with 4 g of dibromantoin in the dark at room temperature for one hour when TLC in 50% ethyl acetate/50% Hexane shows the reaction to be complete. The reaction mixture is precipitated in 2 liters of water, stirred for 10 minutes and the crystalline precipitate is collected by filtration, washed with water, and air dried to give 11.4 g of 6α-fluoro-9α-bromo-11β-hydroxy-16β-methyl-17α,21-diacetoxypregna 1,4-diene-3,20-dione.

This bromohydrin (19.1 g) is mixed with 286 ml of methyl orthoformate, 96 ml of anhydrous methanol and 1.9 ml of fuming sulfuric acid and heated on a water bath at 80°–85° for 15 minutes. The mixture is treated with 15 mls of pyridine and poured into 300 ml of water, separated and washed three times with water, dried over anhydrous sodium sulfate, filtered and concentrated under high vacuum to a foam which is cooled in crushed dry iced for 16 hours to give the 11β-orthoester of 3-methoxy-6α-fluoro-9α-bromo-16β-methyl-17α,21-diacetoxypregna-1,3,5(6)-triene-20-one.

The orthoester so obtained is dissolved in 300 ml of a mixture of 80% THF/20% water and treated at room temperature with a slow stream of perchloryl fluoride until no more starting material is detected by TLC analysis. The mixture is diluted with water and the organic solvent eliminated under reduced pressure (high vacuum) at 80°–85° C. The mixture is diluted with water up to two 1 and kept in the refrigerator for 20 hours. The resulting precipitate is filtered and air dried.

One (1) g of crude reaction mixture is dissolved in about 20 ml of methylene dichloride (MDC) and filtered through a 10 g column of silica with 100% MDC. The column was eluted with 1.2 l of MDC, then with 2% ethyl acetate/98% MDC. The homogeneous fractions containing small amounts of negative and positive polar impurities were concentrated to dryness under a high vacuum. NMR analysis of the negative polar product eluted indicates that the product is 4,6α-difluoro-9α-bromo-11β-hydroxy-16β-methyl-17α,21-diacetoxypregna-1,5(6)-diene-3,20-dione.

The resulting product is mixed with tin tributylhydride in tetrahydrofuran at room temperature to eliminate the 9α-bromine and form 4,6α-difluoro-11β-hydroxy-16β-methyl-17α,21-diacetoxypregna-1,5(6)-3,20-dione (The reaction may be accelerated by adding a small amount of a free radical and refluxing).

The resulting product is stirred with methanol containing anhydrous potassium carbonate under nitrogen at atmospheric pressure and ambient temperature until TLC shows the reaction is complete. The reaction mixture is diluted with methanol and glacial acetic acid and concentrated under reduced pressure to a small volume. The crystalline precipitate which forms is collected by filtration and washed with methanol and water to give 4,6α-difluoro-11β-hydroxy-16β-methyl-17α,21-dihydroxypregna-1,4-diene-3,20-dione.

The resulting product is reacted with aqueous periodic acid (H$_5$IO$_6$) in methanol at room temperature until the reaction is complete as judged by TLC. The methanol is removed by evaporation, water is added and the resultng precipitate removed by filtration and purified by crystallization to give 4,6α-fluoro-11β,17α-dihydroxy-16β-methyl-3-oxoandrosta-1,4-diene 17β-carboxylic acid.

This product is then reacted with an anhydride and pyridine according to the process set forth in Preparation I, Part B to give the corresponding 17α-ester derivative which, in turn, is reacted according to the process of Example 1, Part C to give methyl 4,6α-difluoro-11β-hydroxy-16β-methyl-3-oxo-17-propionyloxyandrosta-1,4-diene 17β-carboxylate;

phenyl 4,6α-difluoro-11β-hydroxy-16β-methyl-3-oxo-17-propionyloxyandrosta-1,4-diene 17β-carboxylate;

benzyl 4,6α-difluoro-11β-hydroxy-16β-methyl-3-oxo-17-propionyloxyandrosta-1,4-diene 17β-carboxylate;

2 fluoroethyl 4,6α-difluoro-11β-hydroxy-16β-methyl-3-oxo-17-propionyloxyandrosta-1,4-diene 17β-carboxylate;

chloromethyl 4,6α-difluoro-11β-hydroxy-16β-methyl-3-oxo-17-propionyloxyandrosta-1,4-diene 17β-carboxylate;

methyl 4,6α-difluoro-17α-hexanoyloxy-11β-hydroxy-16β-methyl-3-oxoandrosta-1,4-diene 17β-carboxylate; and the like.

B. The final compounds resulting from Part A of this example is further elaborated into other compounds of this invention by first forming the corresponding androsta-1,4,9(11)-triene. This is accomplished by any means known in the art such as dissolving benzyl 4,6α-difluoro-11β-hydroxy-16β-methyl-3-oxo-17-propionyloxy androsta-1,4-diene 17β-carboxylate in DMF, adding methylsulfonyl chloride and pyridine and heating at about 80° C. until the reaction is complete. The product is extracted with an organic solvent such as ethyl acetate, washed with water, dried over sodium sulfate and evaporated to yield methyl 4,6α-difluoro-16β-methyl-3-oxo-17α-propionyloxyandrosta-1,4,9(11)-triene 17β-carboxylate. This, in turn, is chlorinated using chlorine in carbon tetrachloride according to methods known in the art to give benzyl 4,6α-difluoro-9α,11β-dichloro-16β-methyl-3-oxo-17α-propionyloxyandrosta-1,4-diene 17β-carboxylate.

What is claimed is:

1. A compound chosen from those represented by the formula

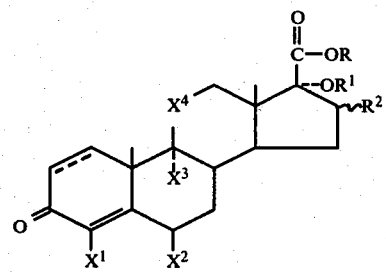

wherein
X$^1$ is fluoro or chloro;
X$^2$ is fluoro, chloro or hydrogen;
X$_3$ is fluoro, chloro, bromo or hydrogen;
X$^4$ is =C=O or

or may be

when X$^3$ is chloro;
R is hydrogen; alkyl of one through six carbon atoms; alkyl of one through six carbon atoms substituted with one halo; phenyl; benzyl; phenyl substituted with alkyl of one through four carbon atoms, alkoxy of one through four carbon atoms or halo; or benzyl substituted on the phenyl ring with alkyl of one through four carbon atoms, alkoxy of one through four carbon atoms or halo;
R$^1$ is hydrogen or alkanoyl of 2 through 6 carbon atoms;
R$^2$ is hydrogen, α-methyl or β-methyl; and
the solid and broken lines between C-1 and C-2 represent a double or a single bond.

2. A compound of claim 1 wherein R$^2$ is α-methyl.

3. A compound of claim 2 wherein R is methyl.

4. The compound of claim 2 wherein R is alkyl of 1 to 6 carbon atoms, phenyl or benzyl and R$^1$ is alkanoyl of 2 through 6 carbon atoms.

5. The compound of claim 4 wherein X$^1$ is chloro, X$^2$ and X$^3$ are fluoro and X$^4$ is

6. The compound of claim 4 wherein X$^1$ and X$^3$ are chloro, X$^2$ is fluoro and X$^4$ is

7. The compound of claim 4 wherein X; X$^2$ and X$^3$ are each fluoro and X$^4$ is

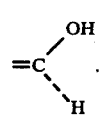

8. The compound of claim 7 wherein R$^2$ is α-methyl, R and R$^1$ are both hydrogen and the bond between C$_1$ and C$_2$ is a double bond, namely 4,6α,9α-trifluoro-11β,17α-dihydroxy-16α-methyl-3-oxoandrosta-1,4-diene 17β-carboxylic acid.

9. The compound of claim 7 wherein R$^2$ is α-methyl, R is methyl, R$^1$ is propionyl and the bond between C$_1$ and C$_2$ is a double bond, namely methyl 4,6α,9α-trifluoro-11β-hydroxy-16α-methyl-3-oxo-17α-propionyloxy-androsta-1,4-diene 17β-carboxylate.

10. A topical anti-inflammatory pharmaceutical composition which comprises a therapeutically effective amount of the compound of claim 1, with the proviso that R is not hydrogen, in combination with at least one suitable pharmaceutical excipient.

11. A process for treating an inflamed condition in a mammal which comprises administering a therapeutically effective amount of the compound of claim 1, with the proviso that R is not hydrogen, to said mammal.

* * * * *